(12) United States Patent
Rettinghaus

(10) Patent No.: US 6,310,340 B1
(45) Date of Patent: Oct. 30, 2001

(54) ARRANGEMENT FOR CONNECTING A LOW-PRESSURE INLET OF A GAS ANALYZER

(75) Inventor: Gerhard Rettinghaus, Balzers (LI)

(73) Assignee: Unaxis Balzers Aktiengesellschaft, Fuerstentum (LI)

(*) Notice: Subject to any disclaimer, the term of this patent is extended or adjusted under 35 U.S.C. 154(b) by 0 days.

(21) Appl. No.: 09/161,472

(22) Filed: Sep. 28, 1998

Related U.S. Application Data

(63) Continuation-in-part of application No. PCT/CH97/00122, filed on Mar. 24, 1997.

(30) Foreign Application Priority Data

Mar. 27, 1996 (DE) .............................................. 296 05 650

(51) Int. Cl.⁷ .................................................. H01J 49/00
(52) U.S. Cl. ......................................................... 250/288
(58) Field of Search ............................. 250/288, 288 A, 250/281, 282

(56) References Cited

U.S. PATENT DOCUMENTS

| | | | |
|---|---|---|---|
| 3,633,027 | 1/1972 | Ryhage . | |
| 4,112,297 | * 9/1978 | Miyagi et al. | 250/288 |
| 4,570,066 | * 2/1986 | Schlag et al. | 250/288 |
| 4,933,548 | * 6/1990 | Boyer et al. | 250/288 |
| 5,318,752 | 6/1994 | Visser . | |

FOREIGN PATENT DOCUMENTS

| | | |
|---|---|---|
| 2 033 954 | 1/1972 | (DE) . |
| 29 39 893 A1 | 4/1980 | (DE) . |
| 0 550 957 A1 | 7/1993 | (EP) . |

* cited by examiner

Primary Examiner—Kiet T. Nguyen
(74) Attorney, Agent, or Firm—Crowell & Moring LLP

(57) ABSTRACT

Arrangement and method for connecting a low-pressure connection of a gas analyzer with a test gas connection operated at a higher pressure level includes a connection line with a connection for the low-pressure connection and a connection for the test gas connection. A gas flow connection leads into the connection line, and a valve body is configured to be operable in the connection line for controlling a gas flow cross-section thereof for the connection to the low-pressure connection. The valve body is guided within a line section connected with the connection line on the gas flow connection, and the gas flow cross-section is formed between an interior wall thereof and the valve body.

10 Claims, 1 Drawing Sheet

ARRANGEMENT FOR CONNECTING A LOW-PRESSURE INLET OF A GAS ANALYZER

CROSS-REFERENCE TO RELATED APPLICATIONS

This application is a continuation-in-part of PCT Application No. PCT/CH97/00122 filed on Mar. 24, 1997.

BACKGROUND OF THE INVENTION

The present invention relates to an arrangement for connecting a low-pressure inlet of a gas analyzer with a test gas connection operated at a higher pressure level, comprising a connection line with a connection for the low-pressure connection as well as a connection for the test gas connection, another gas flow connection leading into the connection line, a valve body which operates in the connection line and controls its gas flow cross-section for the connection to the low-pressure connection, to a mass spectrometer having such an arrangement and to a use of the above-mentioned arrangement and of the mass spectrometer.

As a typical example of the mentioned gas analyzers, mass spectrometers are frequently used, for example, for analyzing gas compositions. Particularly in the case of vacuum treatment processes, such as PVD, PECVD or CVD processes, it is increasingly necessary to precisely control the treatment gas atmosphere particularly for control the treatment gas atmosphere particularly for critical applications. In this case, CVD processes are also used under atmospheric pressure conditions.

The gas analyzers normally operate in vacuum ranges which are much lower, for example, in the $10^{-3}$ bar range, than the process pressures of, for example, 0.1 mbar to 100 mbar, which are used in the above-mentioned processes. The resulting problems during the coupling of the gas analyzers of the above-mentioned type to the test gas atmospheres to be analyzed are known: Falsification of the gas composition when transferring the gas to the analyzer, falsification of the gas composition in the analyzer itself or damage to or at least contamination of the analyzer by the gas to be tested.

This problem becomes worse when the test gas is a reactive gas which may react with solid phases in the connection system and/or at the analyzer, or when such a reactive gas forms solid reaction products which are deposited in the above-mentioned connection system and/or on the input side of the gas analyzer.

Different approaches are known for solving these problems.

For example, a first known approach consists of providing a pressure stage in the form of a screen in the connection line. The providing of such a fixed pressure stage, as known, for example, from U.S. Pat. No. 5,318,752, has the disadvantage that it often cannot utilize the highest possible operating pressure of the gas analyzer. In the case of changing pressures of the gas to be analyzed, a variation possibility of the screen or the pressure stage would therefore be desirable. only in this manner, an optimal relationship can be established in every case between the useful signal and the background signal at the analyzer.

This is ensured by the also known provision of an adjustable leakage valve as the pressure stage. However, the providing of a valve mechanism in the above-mentioned connection system results in serious disadvantages with respect to the enlargement of he gas-absorbing surfaces, the introducing of additional dead volumes with corresponding memory effects, as well as with respect to the contamination of the gas atmosphere, for example, by mechanical abrasion.

The disadvantages of the above-mentioned mechanical leakage valves were eliminated partially by the introduction of the so-called "virtual valves" but without completely retaining the advantages of the mechanical valves. The "virtual valves" are gas-dynamic pressure stages or ends, in the case of which the analysis gas flow to toward the analyzer encounters a barrier gas flow in the counterflow. In the case of a corresponding barrier gas flow, the analysis gas can largely be kept away from the test inlet of the analyzer. In this respect, reference is also made to the above-mentioned U.S. Pat. No. 5,318,752.

The most important disadvantage of the "virtual valves" is the fact that the barrier gas flow does not permit the implementation of a complete locking, as required, for example, when ventilating a process chamber to which the analyzer is connected. In addition, a point is formed at the mouth of the gas inlet for the barrier gas into the connection system at which memory effects may occur. This may take place in that, for example, old gas residues remain adsorbed at the above-mentioned gas inlet, which gas residues later, when the barrier gas is switched off, are desorbed and will falsify analyses which follow.

U.S. Pat. No. 3,633,027 discloses a so-called Becker-Ryhage-Separator on which a pump connection is led by way of an inlet nozzle to the inlet of a gas-phase chromatograph. Opposite an inlet nozzle to the gas-phase chromatograph, an outlet nozzle is provided to a second—a mass spectrometer—stage. A slide, which can be adjusted into two discrete positions, is guided in a guide housing and closes or opens the above-mentioned nozzles.

DE-OS 29 39 893 shows a mass spectrometer acted upon by way of a connection line by two connections, which connection line has a third connection for the mass spectrometer. A valve body operated in the pulse operation in this case controls the flow cross-section from the connection line to the mass spectrometer.

SUMMARY OF THE INVENTION

An object of the present invention to eliminate the above-described disadvantages with respect to memory effects of an arrangement of the latter type. This is achieved by the valve body is guided within a line section connected with the connection line on the additional gas flow connection and the gas flow cross-section of the line section is formed between its interior wall and the valve body.

BRIEF DESCRIPTION OF THE DRAWING

These and further objects, features and advantages of the present invention will become more apparent from the following detailed description of a currently preferred embodiments when taken in conjunction with the accompanying drawing.

The sole FIGURE is a schematic view of a connection arrangement according to the present invention or of a mass spectrometer according to the present invention, preferably a quadrupole mass spectrometer, having a connection arrangement according to the invention.

DETAILED DESCRIPTION OF THE DRAWING

Figure 1:
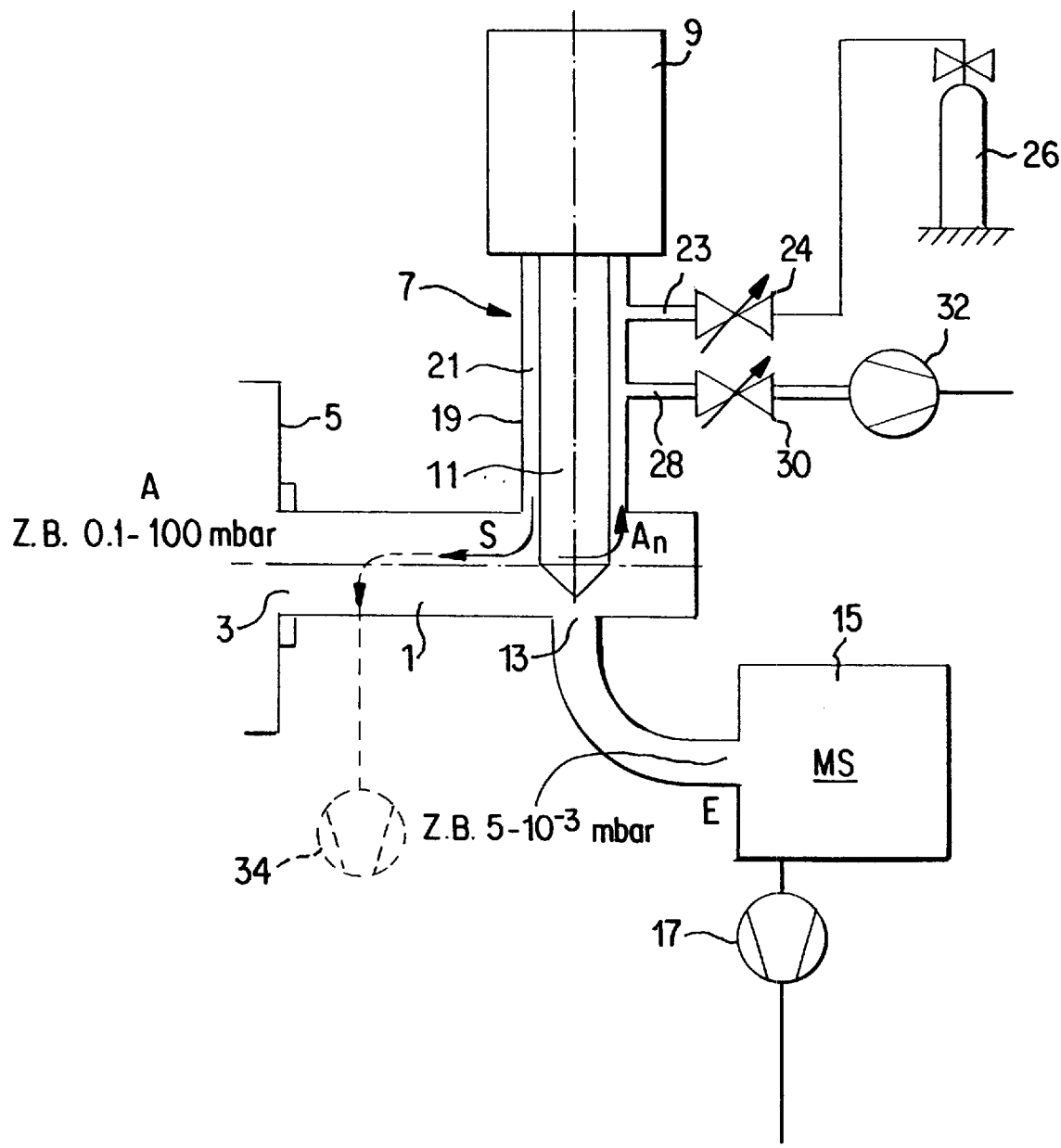

| Definitions: | |
|---|---|
| Test gas | Gas to be analyzed is removed by |
| test gas inlet | way of an inlet from a gas |
| test gas atmosphere | atmosphere. The latter exists in a chamber. The atmosphere |
| test chamber | may preferably be a vacuum atmosphere, such as a process atmosphere of a vacuum treatment process. |
| valve | A valve has a valve body which is |
| valve body | movable in a controlled manner in |
| valve gear | a valve body guide. In this |
| valve body guide | drive, the valve body is driven by the valve gear. |

A test gas inlet 3, in the form a flange or the like for the connection, for example, to a test chamber 5, such as a vacuum treatment chamber, such as, an etching chamber, is provided on a connection line 1, customarily called a "baffle" line. A leakage valve 7 with a drive unit 9 closes in a controlled manner, as a variable pressure stage 13, the flow cross-section of the connection line 1 to the inlet E of a gas analyzer 15, for example, preferably, of a quadrupole mass spectrometer with a connected turbomolecular pump 17. The valve body 11 is movable in a valve body guide 19 and, with respect to the guide 19, defines the line 19. By way of a connection 23 and a control valve 24, this line 21 is connected to a barrier gas tank 26 and, by way of a connection 28 and a control valve 30, is connected to a vacuum pump 32.

Depending on the pressure conditions in the test gas atmosphere A during operation, the pressure stage 13 is adjusted by a more or less extensive restorable of the valve body 11. Simultaneously, by establishing a gas counterflow S by way of the connection 23, the known advantages of a gas counterflow with respect to the partial pressure conditions can be utilized on the inlet side of the gas analyzer. As illustrated by a broken line at reference number 34, an additional pump connection can be provided for this purpose between the gas inlet from the line 21 to the test gas inlet 3. The gas counterflow S prevents the test gas from being absorbed in the area of the volume of line 21 and particularly also in its mouth area in line 1.

Otherwise, by way of connection 28, a test gas flow $A_n$ can also be established by way of line 21 which prevents any return flow from line 21.

In barrier periods in which a complete blocking of inlet E is not required, a correspondingly dimensioned barrier gas flow S prevents penetration of test gas to inlet E of the mass spectrometer 15. The "virtual valve" will then be closed. When a complete blockage is required, for example, for flooding the atmosphere A, the leakage valve with the valve body 11 is closed.

The connection system according to the present invention adapts the pressure in the measuring instrument to the pressure in the test gas atmosphere A, specifically by a corresponding adjustment of the flow cross-section by the leakage valve 7 without having to accept the otherwise customary disadvantages of a leakage valve. Independently of changing test gas pressures, the best possible spacing is therefore always obtained between the partial test gas pressure and the partial residual gas pressure.

By providing the leakage valve 7, the highly sensitive inlet E of the gas analyzer 15 can be blocked even with respect to ambient atmospheric pressure. Even if in this case the valve body 11 does not absolutely ensure a complete closing of the flow cross-section 13, the inlet E can be optimally protected by the simultaneous establishment of a barrier gas flow S.

By the variation of the flow cross-section corresponding to pressure stage 13, estimates of the characteristic background become possible on the analyzer 15, for example, in the case of a mass spectrometer, of its ion source. Memory and leakage effects from the leakage valve volume are avoided by its utilization as a barrier gas line and/or as a pumping line. The known advantages of counterflow measuring processes can be flexibly utilized. The test gas flow through line 1 can be increased by the utilization of line 21 as a pumping line.

If deposits are formed in the pressure stage which reduce the conductance, the previous conductance can be reestablished, optionally also in an automatically readjusting manner, by an adjustment. Thus, the system according to the present invention is also suitable particularly for usages in which the analysis gas has reactive fractions.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. Apparatus for connecting a low-pressure input of a gas analyzer with an input for a test gas to be analyzed, said input for said test gas being operable at a higher gas pressure than permissible for said gas analyzer input, comprising:
   - a connection line interconnecting a connection for said low-pressure input and a connection for said input for said test gas;
   - a gas flow line opening in said connection line and having at least one gas-flow-line-connector remote from said connection line;
   - a valve body configured and arranged to be movable in said gas flow line to control a gas flow cross-section of said connection line between said connection for said low-pressure input and said connection for said input for said test gas; and
   - a gas flow path from said connection line to said gas-flow-line-connector and in said gas flow line being formed between said movable valve body and the inner wall of said gas flow line.

2. The apparatus of claim 1, wherein said at least one-gas-flow-line connector line is connected to one of a gas source and a vacuum pump.

3. The apparatus of claim 1, wherein said at lest one gas-flow-line-connector comprises a first one being connected to a gas source and a second one being connected to a vacuum pump.

4. The apparatus of claim 1, comprising a pump connected to said connection line between said connection for said input for said test gas and said gas flow line opening in said connection line.

5. The apparatus of claim 1, wherein said valve body is operatively configured to controllably vary said gas flow cross-section of said connection line.

6. Mass spectrometer, comprising an apparatus including
   - a connection line interconnecting a connection for low-pressure input and a connection for input for a test gas;
   - a valve body configured and arranged to be movable in said gas flow line to control a gas flow cross-section of said connection line between said connection for said low-pressure input and said connection for said input for said test gas; and a gas flow path from said connection line to said gas-flow-line-connector and in said gas flow line being formed between said movable valve body and the inner wall of said gas flow line.

7. Mass spectrometer according to claim 6, wherein said at least one gas-flow-line connector is connected to one of a gas source and a vacuum pump.

8. Mass spectrometer according to claim 6, wherein said at least one gas-flow-line comprises a first one being connected to a gas source and a second one being connected to a vacuum pump.

9. Mass spectrometer according to claim 6, comprising a pump connected to said connection line between said connection for said input for said test gas, with said gas flow line opening in said connection line.

10. Mass spectrometer according to claim 6, wherein said valve body is operatively configured to controllably vary said gas flow cross-section of said connection line.

* * * * *